US00PP12928P2

(12) United States Plant Patent
Inoue et al.

(10) Patent No.: US PP12,928 P2
(45) Date of Patent: Sep. 10, 2002

(54) SHIITAKE MUSHROOM PLANT NAMED 'HS607'

(75) Inventors: Sadayuki Inoue; Sumio Ayusawa, both of Tochigi; Shigeo Takano, 875-1, Hoshigawauchi, Kamiachimancho, Tokushima-shi, Tokushima 770-8040; Katsumasa Eda; Takahiro Yamauchi, both of Tochigi, all of (JP)

(73) Assignees: Hokken Co., LTD, Tochigi; Shigeo Takano, Tokushima, both of (JP)

( * ) Notice: Subject to any disclaimer, the term of this patent is extended or adjusted under 35 U.S.C. 154(b) by 33 days.

(21) Appl. No.: 09/694,019

(22) Filed: Oct. 23, 2000

(30) Foreign Application Priority Data

Oct. 27, 1999 (JP) ..... 11-12059

(51) Int. Cl.[7] ..... A01H 15/00

(52) U.S. Cl. ..... Plt./394

(58) Field of Search ..... Plt./394

*Primary Examiner*—Bruce R. Campell
*Assistant Examiner*—June Hwu
(74) *Attorney, Agent, or Firm*—Armstrong, Westerman & Hattori, LLP

(57) ABSTRACT

The present invention relates to a new, distinct horticultural variety of shiitake mushroom, *Lentinus edodes* (Berk.) Sing. This new variety, named 'HS607', was found by crossbreeding. It is adaptable to both season-off cultivation on logs and short (forcing) or long (natural) term cultivation on sawdust beds.

9 Drawing Sheets

BACKGROUND OF THE INVENTION

Shiitake mushrooms, *Lentinus edodes* (Berk.) Sing., grow naturally on the dead wood of many hardwood species. In Japan, shiitake mushrooms have been cultivated on bed logs for 300 years, and today cultivation of them is an important agricultural business. In 1997, 75,000 tons of fresh shiitake mushrooms and 6000 tons of dried shiitake mushrooms were produced. Under circumstances where approx. 60% of shiitake mushrooms have been cultivated on logs, conventionally many commercial varieties have been bred for log cultivation.

Sawdust bed cultivation of shiitake mushrooms, which was begun about twenty years ago, is characterized by rapid growth in comparison with log cultivation, and so it is a better method for commercial and mass production. On the other hand, because of limited number of varieties of shiitake suitable for sawdust bed cultivation, frequently those for log cultivation are used instead. However, when these common commercial varieties for log cultivation are cultured on sawdust beds, it takes more than four months to culture, because less than three months culture may cause that either the fruit bodies do not develop, or abnormal fruit bodies without caps appear. Furthermore, in the light of yield, less than three months culture brings a poor yield.

In 1985 the breeders of this invention developed 'Hokken 600' (registration No. 1791 based on the Japanese seed and Seedlings Law). 'Hokken 600' bears normal fruit bodies after only three months culture at 20° C. under general commercial conditions.

Following the development of 'Hokken 600', the object of this breeding is to develop a variety of shiitake adaptable to both season-off log cultivation and sawdust bed cultivation. The breeding process is described below. This breeding project was carried out from 1993 to 1998 in Mibu-machi, Shimotsuga-gun, Tochigi-ken, Japan and Tokushima-shi, Tokushima-ken, Japan.

1. One parent is 'Hokken 600' (registration No. 1791 based on the Japanese seed and Seedlings Law) and the other is 'Hokken 603' (registration No. 4343 based on the same Law). Monokaryotic hypha were isolated from fruit bodies of each parent by monospore separation.

2. Dikaryotic hypha were produced by crossing monokaryon mycelia.

3. These dikaryotic hypha were selected first on the basis of the degree of mycelial growth on PDA-media in Tokushima-shi.

4. The selected dikaryotic hypha were cultivated on sawdust media in Tokushima-shi. Finally, this new variety of shiitake mushroom was selected by evaluating the desirable cultivation characteristics.

5. At the same time, the selected dikaryotic hypha was cultivated on logs both in Tokushima-shi and in Mibu-Machi for four years, and this shiitake mushroom was proved adaptable to log cultivation as well.

This shiitake mushroom was cultured confronting with forty-nine varieties of commercially cultivated shiitake mushrooms, including the parent varieties, on PDA-media. The results showed that this shiitake mushroom formed zone lines between all varieties (but the result of culture between 'Hokken 603' was only pseudo-positive.), and proved to have genetic sex factors different from those of all forty-nine varieties.

The clones or propagules of the claimed plant are identical to the original plant in all distinguishing characteristics.

To study the properties of this shiitake mushroom, sawdust bed cultivation was conducted under the following conditions: culture at 20° C., for 100 days; and development at 13° to 18° C. (a cycle of 12 hours) in 70 to 90% humidity for 80 days. Bag cutting was used for the first flush or break treatment, and soaking for the second, third and fourth treatments.

Changes in yield of the present shiitake mushroom developed by the first, second, third and fourth treatments is shown in FIG. 4 comparing with 'Hokken 600' and 'Hokken 603' as control varieties, which are for sawdust bed cultivation.

This shiitake mushroom yielded 416.3 grams of fruit bodies per bag of 1.2 kg sawdust bed and was confirmed to be suitable for sawdust bed cultivation. The number of days required between the beginning of development and the stage of peak development of this shiitake mushroom was eight days, which shows the same level as 'Hokken 600' and 'Hokken 603'.

This shiitake mushroom can be asexually reproduced by subculture for a given period of time. The subculture is a common method for maintaining a mushroom strain on suitable media. Media such as PDA (potato dextrose agar) and MEA (malt extract agar) can be used as shiitake culture media, and shiitake strain can be subcultured every one to six months. To produce a spawn, fragments of the dikaryonicic mycelia grown on PDA or MEA are inoculated in sawdust or wood media, and are cultured at about 20 for one to three months. Sawdust spawn is used on sawdust beds, and sawdust or wood chip spawn is used for logs in commercial cultivation.

SUMMARY OF THE INVENTION

The outstanding characteristics of this shiitake mushroom in its cultivation on sawdust beds are: that the culture period and the number of days required until the peak development stage are equivalent to those of the standard varieties; that its yield per bag of sawdust bed is increased; and that the quality of the fruit bodies is very good.

BRIEF DESCRIPTION OF THE DRAWING

FIG. 1 shows a top view of the fruit body of the shiitake mushroom of the present invention.

FIG. 2 is a bottom view of the fruit body of the shiitake mushroom of the present invention.

FIG. 3 is a side (cross section) view of the fruit body of the shiitake mushroom of the present invention.

FIG. 5 shows the laying yard of logs for cultivation.

FIGS. 6 and 7 show the third development of this shiikate mushroom on beg logs.

FIGS. 8 and 9 show the culture and development of this shiitake mushroom on sawdust beds.

BOTANICAL DESCRIPTION

Figure 4:
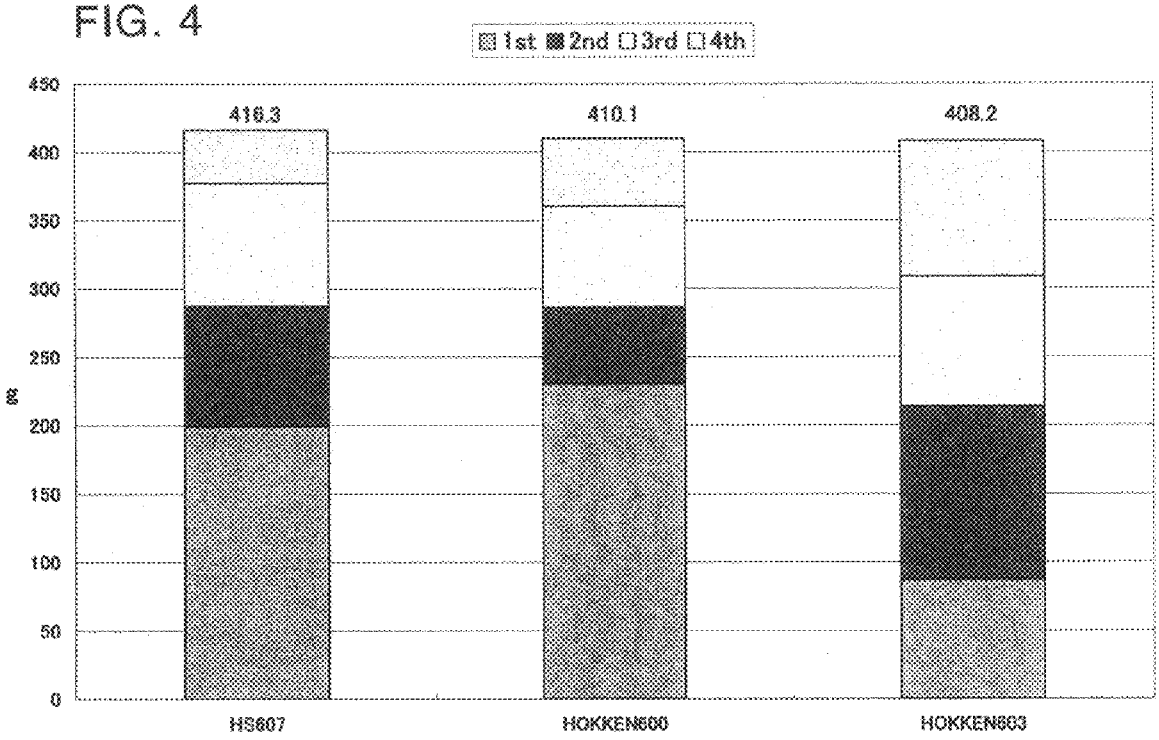
FIG. 4 illustrates the yield of the shiitake mushroom of the present invention 'HS607' in sawdust bed cultivation. 'Hokken 600' and 'Hokken 603' were used as the control varieties. The following conditions were used: 20 and 100 days for culture; 13 to 18 (a cycle of 12 hours) and 70 to 90% humidity for development. For the first flush or break treatment bag cutting was used, then for the second, third and forth treatments soaking was used.

The following detailed description of the shiikate mushroom of the present invention is given with reference to the Munsell Book of Color 1976, and Japanese standards of examination for shiitake mushrooms. This description is of the fruit body grown under commercial conditions. When grown under different conditions, it will be obvious that its appearance may be different from that described.

The age of the observed plant was approximately 165 days (65 days inoculum period and 100 days culture period).

The cap or pileus of this fruit body is of a convex shape near to flat when immatured, and changes to a flat shape when matured. Cap diameter of the mature fruit body is 35.6 mm to 88.9 mm, with an average of 67.2 mm, which is slightly bigger than the standard type. The color of the cap is 7.5YR7/2 and 7.5YR3/4. The flesh of the cap is 10.1 to 19.1 mm in thickness, averaging 13.7 mm, which is the ordinary thickness of the standard type. The flesh texture is normal.

Scales cover the entire surface of the cap, specially concentrating around the outer edges. The scale color is 10YR9/2.

The arrangement of gills or lamellae is normal. The gill width is 3.0 to 5.5 mm, with an average of 4.1 mm, which is narrower than the standard type. The gill color is 2.5Y9/4.

The length of the stem or stalk is between 29.8 and 78.9 mm, with an average of 55.8 mm, slightly longer than the standard type. The stem thickness is between 8.0 and 21.1 mm, the average being 14.3 mm, which is roughly the same as the standard type. The color of stem is 10YR9/1. The stem is covered with hair without volva. The color of the hair is 5YR9/4.

The ratio of the cap diameter to the stem length is 0.9–1.6, the average being 1.2.

The resistance of 'HS607' to harmful bacteria, Trichoderma and Penicillium, is higher than that of 'Hokken 600' and 'Hokken 603'.

What is claimed is:

1. A new, distinct variety of shiitake mushroom plant as substantially illustrated or described in the specification.

* * * * *